US00PP26138P3

(12) United States Plant Patent
Van Rosmalen

(10) Patent No.: US PP26,138 P3
(45) Date of Patent: Nov. 24, 2015

(54) ***PHALAENOPSIS* ORCHID PLANT NAMED 'PHALCUWIM'**

(50) Latin Name: ***Phalaenopsis* hybrid**
Varietal Denomination: PHALCUWIM

(71) Applicant: ANTHURA B.V., Bleiswijk (NL)

(72) Inventor: Nicolaas Arnoldus Maria Van Rosmalen, Velp (NL)

(73) Assignee: ANTHURA B.V., Bleiswijk (NL)

( * ) Notice: Subject to any disclaimer, the term of this patent is extended or adjusted under 35 U.S.C. 154(b) by 288 days.

(21) Appl. No.: 13/986,990

(22) Filed: Jun. 21, 2013

(65) Prior Publication Data

US 2014/0380539 P1 Dec. 25, 2014

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

U.S. PATENT DOCUMENTS

PP25,510 P3 * 5/2015 Van Rosmalen ..... Plt./311

OTHER PUBLICATIONS

Anthura Unlimited in Varieties Phalaenopsis Pot Plant Culture 2012, pp. 1-52.*
Enclosure for the Plant Patent application of Anthura BV, 13 pages 2015.
Anthura Phalaenopsis: Cut flower and pot plant culture, 2012, pp. 1 and 50.
Anthura Phalaenopsis: Pot plant culture, 2014, pp. 1 and 50.
EU Community Plant Variety Rights, Official Gazette, Feb. 2013, Apr. 15, 2013, pp. 37 and 59.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALCUWIM', particularly characterized by yellow flowers with yellow-white lip, 2 to 3 peduncles, a short and sturdy inflorescence, a narrow obovate leaf shape, and propagated by tissue culture is disclosed.

3 Drawing Sheets

Genus and species: *Phalaenopsis* hybrid.
Variety denomination: 'PHALCUWIM'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALCUWIM'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALCUWIM' is particularly characterized by its attractive and unique yellow flowers, economical propagation by tissue culture, rapid growth, and a plant dimension suitable for packaging and shipping to the market, and suitable for both 9 cm and 12 cm pot size.

'PHALCUWIM' is a product of a planned breeding program conducted in Bleiswijk, The Netherlands.

The new *Phalaenopsis* 'PHALCUWIM' originated from a cross made in June 2003 in Bleiswijk, The Netherlands. The female parent is a yellow *Phalaenopsis* pot plant name '01-0272' (unpatented), while the male parent is a white *Phalaenopsis* pot plant named '01-0863' (unpatented). A single plant was selected in June 2006 and has been asexually reproduced repeatedly by meristem tissue culture in Bleiswijk, The Netherlands over a 6-year period. The new variety has been found to retain its distinctive characteristics through successive asexual propagations.

Asexual reproduction of 'PHALCUWIM' by meristem tissue culture was first performed in May 2009 in Bleiswijk, The Netherlands and has demonstrated that the new cultivar is firmly fixed and retained through successive generations of asexual reproduction.

Plant Breeder's Rights for this variety have been applied for in Europe on Jan. 15, 2013. 'PHALCUWIM' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Yellow flower with yellow-white lip;
2) 2 to 3 peduncles;
3) Inflorescence is short and sturdy;
4) The shape of the leaf is narrow obovate; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 40-week old plant grown in a greenhouse in Bleiswijk, The Netherlands in May 2013.

DESCRIPTION OF THE NEW VARIETY

Figure 1:
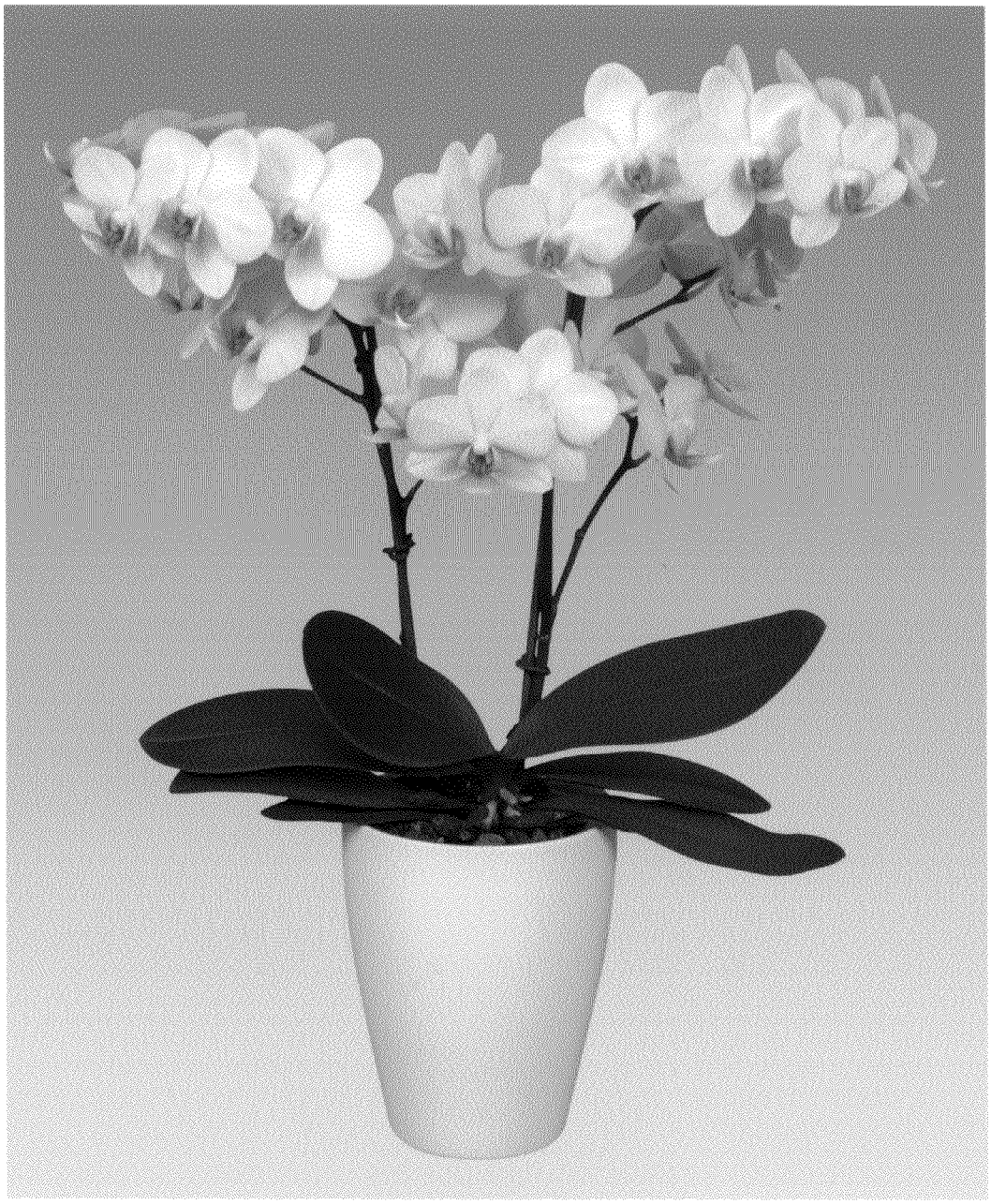
FIG. 1 shows the overall plant habit, including blooms, buds and foliage of 'PHALCUWIM'.
Figure 2:
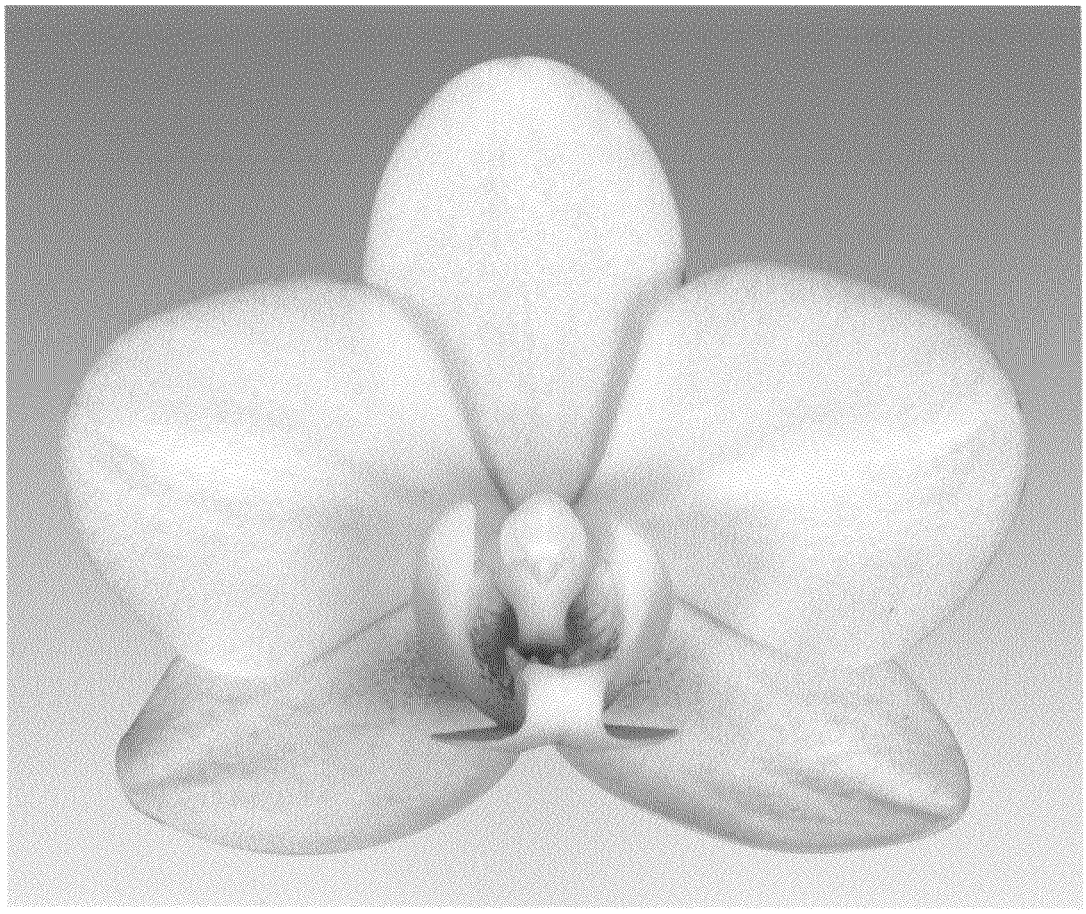
FIG. 2 shows a close-up of the flower of 'PHALCUWIM'.
Figure 3:
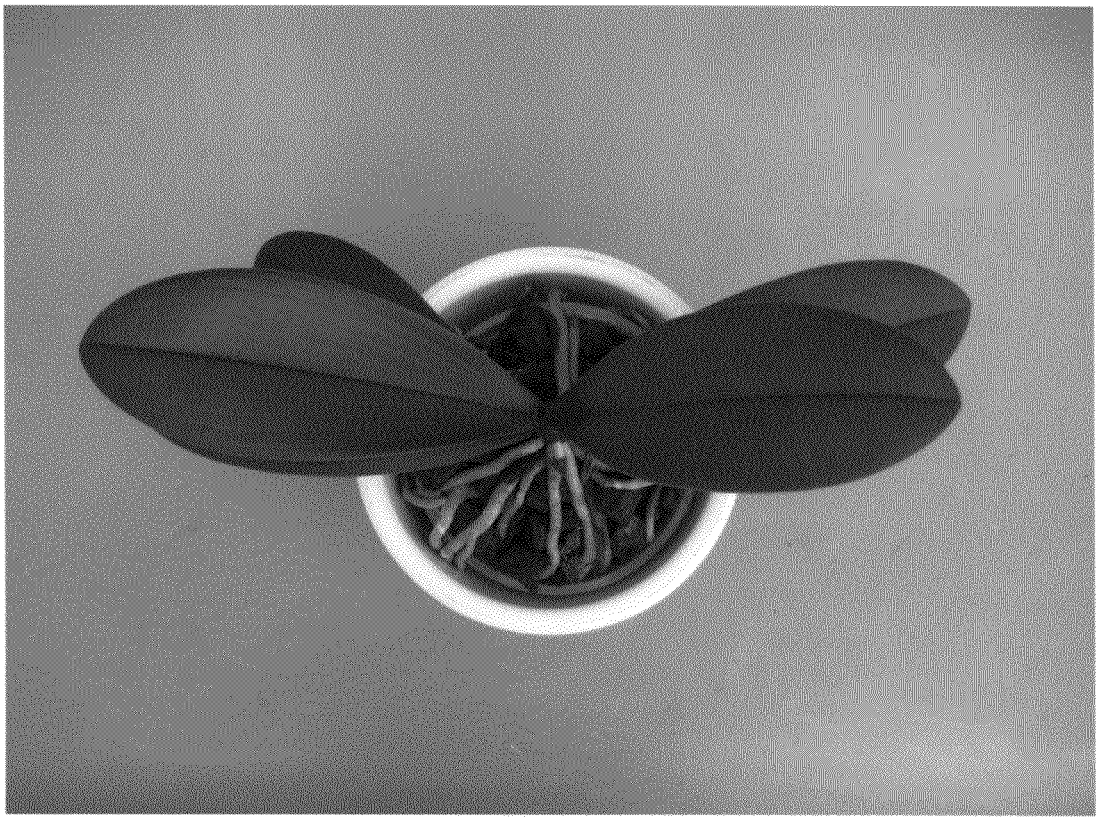
FIG. 3 shows a close-up of the leaves of 'PHALCUWIM'.

The following detailed description sets forth the distinctive characteristics of 'PHALCUWIM'. The data which define these characteristics were collected from asexual reproductions carried out in Bleiswijk, The Netherlands. The plant history was taken on 40-week old plants which were planted from tissue culture in 9 centimeter pots and grown in a greenhouse between 27° C. to 29° C. for 20 weeks, continued by a cooling period of 8 weeks between 18° C. to 20° C. and 12 weeks in a greenhouse of 21° C. Observations were made in May 2013. Color readings were taken under 4000 till 6000 lux natural light in the greenhouse. Color references are primarily to The R.H.S. Colour Chart of The Royal Horticultural Society of London (R.H.S.) (1995).

DETAILED BOTANICAL DESCRIPTION

Classification:

*Family*.—Orchidaceae.

*Botanical*.—*Phalaenopsis* hybrid.

*Common name*.—*Phalaenopsis*.

*Variety name*.—'PHALCUWIM'.

Parentage:

*Female parent*.—*Phalaenopsis* cultivar '01-0272' (unpatented).

*Male parent*.—*Phalaenopsis* cultivar '01-0863' (unpatented).

Propagation:

*Type*.—Meristem tissue culture.

Plant:

*Crop time* (*time to produce a finished flowering plant*).—38 to 40 weeks for a 9 cm pot and 48 to 50 weeks for a 12 cm pot.

*Growth habit of inflorescence*.—Standard type, green leaves and panicle.

*Height* (*including pot, including inflorescence*).—30.0 cm to 40.0 cm.

*Width* (*measured from leaf tips*).—25.0 cm to 30.0 cm.

*Vigor*.—Moderate.

Roots:

*Root description*.—Grey-green-colored roots with light branching lateral roots having grey-green-colored root tips.

Leaves:

*Mature leaves*.—Quantity per plant: 5 to 6 leaves are produced before flowering. Length (fully expanded): 14.0 cm to 16.0 cm. Width: 6.0 cm to 7.0 cm. Shape: Narrow obovate. Apex: Mucronate. Leaf blade angle with the petiole: Between 15 degrees and 30 degrees. Leaf margin: Entire. Color: Upper surface: RHS 147A. Lower surface: A mix of green (RHS 137B) and brown (RHS 200A). Texture: Smooth. Thickness: 1.8 mm. Venation: Pattern: Parallel. Color of the midvein: Upper surface: RHS 187A. Lower surface: RHS 200A.

Peduncle:

*Quantity per plant*.—2 to 3.

*Number of flowers per peduncle*.—10 to 20.

*Length*.—25.0 cm to 35.0 cm.

*Diameter*.—About 0.4 cm.

*Strength*.—Strong.

*Aspect*.—Upright.

*Texture*.—Smooth.

*Color*.—Brown (RHS 200A).

*Internode length*.—50.0 mm to 70.0 mm.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 60.0 mm to 100.0 mm. Diameter: 110.0 mm to 130.0 mm.

*Flowering time*.—First flowers can be expected 7 to 8 months after planting in a 9 cm pot and 10 to 11 months after planting in a 12 cm pot.

*Flower*.—Height: 55.0 mm to 60.0 mm. Diameter: 60.0 mm to 65.0 mm. Depth of lip: 18.0 mm to 20.0 mm.

*Flower longevity*.—On the plant: 10 to 12 weeks.

*Fragrance*.—Absent.

*Petals*.—Arrangement: Open. Shape: Semi-circular. Apex: Rounded. Margin: Entire. Length: 26.0 mm to 28.0 mm. Width: 27.0 mm to 29.0 mm. Color (when fully opened): Upper surface: Basic color: Yellow (RHS 4D). Over color: Light pink center (RHS 78D). Lower surface: Basic color: Yellow-green (RHS 145D).

*Dorsal sepal*.—Shape: Elliptic. Length: 30.0 mm to 32.0 mm. Width: 20.0 mm to 22.0 mm. Color (when fully opened): Upper surface: Basic color: Yellow (RHS 4D). Over color: Light pink center (RHS 78D). Lower surface: Basic color: Yellow-green (RHS 145C to 145D).

*Lateral sepals*.—Shape: Ovate. Length: 19.0 mm to 21.0 mm. Width: 29.0 mm to 31.0 mm. Color (when fully opened): Upper surface: Yellow (RHS 4D and 145D) with red spots towards the center (RHS 53A). Size of spots: Small. Number of spots: Few to medium. Lower surface: Yellow-green (RHS 145C to 145D).

*Labellum* (*lip*).—Margin: Entire. Length: 16.0 mm to 18.0 mm. Width: 14.0 mm to 16.0 mm. Pubescence: Absent. Whiskers: Length: 0.4 cm to 0.6 cm. Color: Yellow (RHS 7A).

*Lateral lobe*.—Length: 1.6 cm to 1.8 cm. Width: 0.8 cm to 1.0 cm. Shape: type IV (as described in the International Union for the Protection of New Varieties of Plants (UPOV) Test Guidelines for *Phalaenopsis*); weakly spatulate Color: White (RHS 155C) and yellow on one side (RHS 12A to 12B) with red stripes towards the callus (RHS 53A) surrounded by few spots (RHS 53A). Size of spots: Small. Number of spots: Few.

*Apical lobe*.—Length: 2.0 cm to 2.2 cm. Width: 1.7 cm to 1.9 cm. Shape: Elliptic. Color: White with yellow-green shade (RHS 155C, 12A to 12B).

*Callus*.—Size: Small. Height: 0.4 cm. Length: 0.4 cm. Width: 0.3 cm. Color: Orange with brown spots (RHS 23A, 172C).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 8.0 mm to 9.0 mm. Diameter: 5.0 mm to 6.0 mm. Color: White (RHS 155C).

*Pollinia*.—Quantity: 2. Size: 1.0 mm to 1.1 mm. Color: Orange (RHS 21B).

*Ovary*.—Length: 9.0 mm to 10.0 mm. Diameter: 4.0 mm to 5.0 mm.

*Pedicel*.—Length: 28.0 mm to 32.0 mm. Diameter: 2.0 mm to 3.0 mm. Color: Green (RHS 144A) and lighter green towards the flower (RHS 145C and 145D).

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

When 'PHALCUWIM' is compared to female parent '01-0272' (unpatented), 'PHALCUWIM' has a smaller flower and shorter whiskers than '01-0272'. Additionally, 'PHALCUWIM' has an elliptic apical lobe of the lip, whereas '01-0272' has a trullate apical lobe of the lip.

When 'PHALCUWIM' is compared to male parent '01-0863' (unpatented), 'PHALCUWIM' has a yellow flower and a weakly spatulate lateral lobe shape, whereas '01-0863' has a white flower and an oblong lateral lobe shape. Additionally, 'PHALCUWIM' has larger flowers and longer whiskers than '01-0863'.

When 'PHALCUWIM' is compared to commercial variety 'Salerno'(unpatented), 'PHALCUWIM' has a yellow flower with a center, an orange callus with brown spots, and an elliptic apical lobe shape, whereas 'Salerno' has a yellow-green flower that is even, a yellow callus with red spots, and a trullate apical lobe shape. Additionally, 'PHALCUWIM' has longer whiskers that 'Salerno'.

I claim:

1. A new and distinct variety of *Phalaenopsis* plant named 'PHALCUWIM' as illustrated and described herein.

* * * * *